United States Patent [19]

Easton et al.

[11] Patent Number: 4,614,794

[45] Date of Patent: Sep. 30, 1986

[54] PROTEIN/POLYSACCHARIDE COMPLEXES

[75] Inventors: Ian A. Easton; Stephen D. Gorham, both of Glasgow, Scotland

[73] Assignee: Johnson & Johnson, New Brunswick, N.J.

[21] Appl. No.: 653,619

[22] Filed: Sep. 24, 1984

[30] Foreign Application Priority Data

Oct. 4, 1983 [GB] United Kingdom ............... 8326542

[51] Int. Cl.⁴ .................... C08H 1/00; C08H 1/06; A61L 27/00
[52] U.S. Cl. .................... 530/356; 530/353; 426/656; 426/657; 426/658
[58] Field of Search ............. 3/1; 128/DIG. 8, 335.5, 128/155; 260/112 R, 123.7, 112 G; 426/656, 657, 658

[56] References Cited

U.S. PATENT DOCUMENTS

| | | | |
|---|---|---|---|
| 3,494,772 | 2/1970 | Bradshaw et al. | 426/277 |
| 3,829,587 | 8/1974 | Tolstoguzov et al. | 426/656 |
| 4,060,081 | 11/1977 | Yannas et al. | 128/DIG. 8 |

FOREIGN PATENT DOCUMENTS 2023384  10/1972  Japan .

*Primary Examiner*—John Kight
*Assistant Examiner*—Nathan M. Nutter

[57] ABSTRACT

Complexes of polyanionic plant polysaccharides with biodegradable proteins, or proteolytic degradation products thereof, are useful in the formation of wound dressings and surgical implants, such as sutures, blood vessel grafts, and artificial organs. The biodegradable protein is preferably collagen, and the polysaccharide is preferably sodium alginate. The complexes are preferably formed by combining the protein and the polysaccharide at a pH which is no higher than the isoelectric point of the protein. The complexes may be crosslinked, such as by dehydrothermal crosslinking or by the use of chemical crosslinking agents such as aldehydes or carbodiimides. Multivalent cations may also be incorporated in the complex in order to give added strength.

14 Claims, No Drawings

PROTEIN/POLYSACCHARIDE COMPLEXES

This invention relates to protein/polysaccharide complexes which are especially useful in the medical and pharmaceutical fields.

It is proposed in British Patent Specification No. 1515963 to form complexes of collagen with polysaccharides of animal origin, such as hyaluronic acid, chondroitin 4-sulphate, chondroitin 6-sulphate, dermatan sulphate, keratan sulphate and heparin sulphate. Such complexes are said to have properties which render them suitable for a wide variety of medical and surgical applications. Specification No. 1515963 teaches the use only of animal polysaccharides which contain hexosamine residues.

Unexpectedly, in view of the teaching of Specification No. 1515963, we have now found that protein/polysaccharide complexes with properties especially useful in the medical and pharmaceutical fields can be formed using certain plant polysaccharides. Such polysaccharides do not contain the hexosamine residues which are present in all the polysaccharides taught in Specification No. 1515963. Moreover, we have found that proteins other than collagen may be used in the formation of useful protein/polysaccharide complexes.

According to the present invention there is provided a process for forming a protein/polysaccharide complex, said process comprising treating a biodegradable protein, or a hydrolytic degradation product thereof, with a polyanionic plant polysaccharide at a pH which is no higher than the isoelectric pH of said protein or degradation product.

According to a further aspect of the present invention there is provided a porous complex of a biodegradable protein, or a proteolytic degradation product thereof, with a polyanionic plant polysaccharide.

The present invention also provides a wound dressing (for example, an artificial skin) having a wound contacting layer formed from a complex of a biodegradable protein, or a proteolytic degradation product thereof, with a polyanionic plant polysaccharide, and also a surgical implant formed from such a complex. Included in the term "surgical implant" are sutures, blood vessel grafts, artificial organs, soft tissue implants and protheses.

The preferred biodegradable protein is collagen, but other proteins such as fibrin or elastin may be used. The biodegradable protein may be used in the process in any of a variety of forms. For example, the protein may be used in the form of intact protein fibres, as solubilised protein, or as partially hydrolysed protein.

Collagen fibres may be prepared by processes known per se, for example the process described in British Patent Specification No. 1,204,438. Briefly, this process involves salting bovine hides for a minimum of 4 days, and preferably for a period of 2 to 4 weeks, following which they are washed in order to remove the salt and to allow them to replump. The hides are then treated in a diliute solution of sodium sulphide in a suspension of lime. After a suitable treatment period, for example 13 hours, the hides are washed to remove the sulphide liquors and replaced in a bath of a saturated lime solution, for a period of 48 hours. On removal from this bath, the hides are fleshed, that is passed through a machine which slices off all adventitious adipose and loose connective tissue. The hides are then resuspended in a second bath of saturated lime solution for a period of 24 hours. After this period, the hides are plump and turgid and can be split through their thickness into a surface or grain layer and into an inner flesh layer, the corium, which is collagen-rich. The corium is then re-fleshed in order to ensure maximum physical cleanliness of this portion of the hide and then further washed. The resulting so-called "splits" are then treated with dilute sodium citrate/citric acid buffer, in order to reduce the calcium content of the splits to a low level, after which the splits are ground to a pulp in water using a conventional meat grinder. This pulp is then suitable for use in the process of the present invention, although it may be freeze-dried for storage if desired.

Solubilised collagen may also be made by processes known per se, such as by the processes described in British Patent Specifications Nos. 990276 and 1184502. The product of these processes is not strictly a soluble collagen, but is probably a microgel and a mixture of several orders of aggregations of the collagen.

Hydrolysed collagen is preferably obtained by the action of trypsin on collagen to yield a polydisperse mixture of polypeptides having molecular weights ranging from approximately 5,000 to 70,000. The collagen should be denatured, for example by heating, prior to the treatment with trypsin. Hydrolysed fibrin and elastin may be prepared using fibrinase and elastase respectively.

Soluble elastin (tropoelastin) may be prepared as follows from aortas of pigs reared on a copper-free diet (Sandberg, L. B., Wolt, T. B., "Methods in Enzymology" 82, 657–665, Ed. Cunningham L. W. & Fredericksen D. W., Academic Press 1982). Briefly, the pigs are killed after 15–17 weeks, the aortas removed and stored deep frozen at −70° C. until required. The aortas are then thawed, cut into strips, frozen in liquid nitrogen and finely ground. The minced tissue is homogenised in a Waring Blender in a buffer solution at pH 7.0 containing 0.5 mM ammonium acetate, 25 mM EDTA, 5 mM N-ethylmaleimide and 1 mM diisopropylfluorophosphate (DFP). The homogenate is centrifuged, the supernatant separated, to which 1 mM DFP is added at hourly intervals while the residue is re-extracted and centrifuged. The combined supernatants are filtered after the addition of 1 mM DFP. Ammonium sulphate is added to 45% saturation and 1 mM DFP again added. After standing overnight, the ammonium sulphate precipitate is resuspended in 0.1M ammonium formate containing 1 mM DFP and dialysed overnight against 0.1M ammonium formate. The dialysed solution is again treated with DFP and the molarity of the ammonium formate increased to 0.5. 1½ vols. of n-propanol are added with continual stirring followed by 2.5 vols. of n-butanol. The precipitate is removed by filtration and the excess solvent flash evaporated. The damp protein residue is treated with chloroform to remove lipids, dried, and re-dissolved in 0.02M formic acid containing 1 mM DFP and dialysed against formic acid overnight. The dialysed solution is then centrifuged to remove any particulate matter and freeze-dried. If desired, the soluble elastin may be further purified by gel filtration on Sephadex G75 in 0.01M pyridine acetate pH 4.9.

It is particularly preferred that the polyanionic plant polysaccharide is an alginate, for example sodium alginate. Among the advantages of using alginate are its cheapness and ready availability, its non-toxicity and non-antigenicity, and the fact that its solubility in vivo can readily be varied by altering the proportion of multivalent cations (for example, calcium ions) in the complex.

Other polyanionic plant polysaccharides may, however, be used in place of alginates. Such polysaccharides may be in their naturally occurring form, or they may be modified. Examples of suitable polysaccharides are carrageenans, celluloses such as carboxymethyl cellulose, xanthan gum and sulphate dextrans. These polysaccharides should be as pure as possible, in order to avoid the inflammatory reactions which are occasionally observed when complexes comprising plant polysaccharides, especially carrageenans, are applied to wound surfaces.

When hydrolysed protein is used to form a complex according to the invention, it is necessary to include a multivalent cation to assist in stabilising the complex. Obviously, when it is desired to use the complex in the medical, pharmaceutical or foodstuffs fields, the multivalent cation must be non-toxic. Suitable multivalent cations include aluminium and calcium ions, of which calcium ion is preferred.

The multivalent cation will usually be present in an amount less than 10% by weight of the complex, and more usually less than 5% by weight, for example 1% by weight.

The use of multivalent cations to assist in stabilising protein/polysaccharide complexes is not restricted to complexes formed from hydrolysed proteins. Such cations, especially calcium ions, may be used to strengthen complexes formed from other fibrous proteins, for example intact collagen fibres and solubilised collagen.

If desired, the protein/polysaccharide complexes of the invention may be crosslinked. Suitable methods of crosslinking include dehydrothermal crosslinking, and the use of aldehydes (such as glutaraldehyde or formaldehyde) or carbodiimides. Whether or not crosslinking is used will depend on the proposed end use of the product. Crosslinking increases the mechanical strength, and decreases the susceptibility of the complex to enzymic degradation. Accordingly, a crosslinked complex may be used to form a relatively non-biosorbable wound dressing, whereas a non-crosslinked complex may be used to form a biosorbable dressing. Suitable crosslinking procedures are described in British Patent Specification No. 1515963.

The complexes of the invention will usually be formed as a precipitate from an aqueous medium. The complexes can be dried under atmospheric conditions and, prior to drying, may be spread to form films. Alternatively, the complexes, particularly where alginates are employed as the carbohydrate component, may be washed in an organic solvent such as acetone or a combination of ethanol and ether, and dried under vacuum. This procedure yields a very fibrous material.

Alternatively, the complexes may be formed into sponge-like structures by blast freezing and replacing the frozen water with a suitable organic solvent.

Preferably, however, the water is removed by freeze-drying. By this technique, sponge-like materials of controlled pore size can be produced. It is particularly preferred that the complexes be blast-frozen before freeze-drying, so that ice crystals formed during the process are of minimal size. This is desirable because large ice crystals may disrupt the pores and result in irregular pore size.

The pore size of material which is to be used as a wound contact layer should preferably be greater than 20$\mu$, and more preferably greater than 50$\mu$, to allow the penetration of fibroblasts into the matrix.

Even larger pore sizes, such as 100$\mu$, are desirable if the material is to be used as a component of a burn dressing, sine high moisture vapour permeability is required in this case.

The physical characteristics of the product may be varied not only by selection of appropriate drying conditions, but also by controlling the solids content of the solution from which the complex is formed. It has been found that the lower the solids content, the thinner the films which can be formed on drying, the greater the flexibility of the resulting film, and the greater the pore size of the product is freeze-dried.

It is preferred that the complex of the present invention be formed from a solution containing less than 2% w/v of protein or solubilised protein, more preferably less than 1% w/v, and most preferably less than 0.5% w/v, e.g. 0.3 to 0.35% w/v. However, considerably higher concentrations of protein degradation products may be used. For example, trypsin-hydrolysed collagen may be used in concentrations up to 25% w/v.

The proportion of protein to polysaccharide can vary considerably, especially where insoluble protein is employed. However, it is preferred that the protein constitutes from 50 to 90% by weight of the complex, for example 50 to 80% by weight.

Protein/polysaccharide complexes according to the present invention and methods of preparing the same, are now described by way of illustration in the following Examples 1 to 3.

EXAMPLE 1

Lyophilised collagen pulp, prepared from bovine hide as described above, was defatted with several changes of either petroleum ether (b.p. 60°–80° C.) or chloroform. Any excess solvent was subsequently removed under reduced pressure.

Suspensions of the collagen so obtained at concentrations up to 0.75% w/v were prepared in either mild acetic acid or a citrate phosphate buffer solution at pH 3–3.2, and homogenised in a Waring Blender until constant turbidity (as measured at 440 nm) was reached (approx. 90 sec.).

After degassing under vacuum, a 1% solution of sodium alginate in mild acetic acid was added to the collagen dropwise from a burette, with continual stirring, until the desired alginate:collagen ratio was reached. The preparation were carried out at room temperature and samples containing 1%, 5%, 10%, 15%, 20% and 25% alginate based on the total weight of collagen were prepared. The collagen/alginate complexes formed as fibrous precipitates, which were then homogenised for 60 sec. in a Waring Blender. After degassing under vacuum, the materials were blast frozen and freeze dried. 1 liter suspension was freeze dried in a tray 11×27 inches (27.9×68.6 cm).

Samples of the composite materials so produced were further stabilised by heating under vacuum for 48 hr. at 115° C.

It was found that such dehydrothermally crosslinked complexes were markedly more stable to soaking in buffered saline solution at pH 7.0. Approx. 50% of alginate component of crosslinked complex remained bound to the collagen after 7 hrs. of soaking, whereas untreated complexes were almost completely dissociated.

Increased stability of the complexes could also be achieved by treatment with crosslinking agents such as aldehydes, multivalent cations or carbodiimides before drying.

EXAMPLE 2

Complexes were prepared by a similar method to that described in Example 1, but using solubilised collagen. To solubilise the collagen, ground bovine hide was soaked overnight in a solution of sodium sulphate (approximately 10% w/v) and then sufficient 10M sodium hydroxide solution was added to bring the final concentration to 2M. After two days, the liquors were removed and the treated hide thoroughly washed in water. Citric acid solution was then added to solubilise the collagen so that the final mixture contained 1.5% by weight collagen and 3% w/v citric acid. The resulting suspension had a pH of around 3.0 and could be diluted to the desired protein concentration with water.

To such material, a solution of sodium alginate was added as described in Example 1 and the resulting complexes freeze dried. Such complexes may be further stabilised by heat treatment and crosslinking (see Example 1) and, alternatively, may be allowed to dry under atmospheric conditions, may be spread out to form films, or may be dried with organic solvents such as alcohol and ether.

EXAMPLE 3

Preparation of protein/polysaccharide complexes using hydrolysed collagen.

A trypsin hydrolysate of collagen, comprising a polydisperse mixture of polypeptides having molecular weights ranging from 5000 to 70000 was dissolved in water to yield a solution of pH 7.5 to 8.0 containing approximately 20% solids. Calcium ion was added to a concentration of approximately 2000 ppm, followed by one quarter the volume of a 2.5% aqueous solution of sodium alginate or pectin. The mixture was then blended in a high speed shear mixer, and the residue washed by resuspending in distilled water and recentrifuging three times.

The material, which was allowed to dry under atmospheric conditions, was strong and stable both at room temperature and at boiling point in 1M sodium hydroxide, 1M hydrochloric acid, and 1M sodium chloride.

The complexes according to the invention are suitable for use in a number of applications in the medical and pharmaceutical fields. Examples of such applications include use as artificial skin, wound dressings, absorbents, insulating materials, or media to be used in the controlled release of physiologically active compounds. Films formed of the complexes of the present invention may be laminated to other materials, for example materials having a controlled degree of moisture vapour permeability, to form an artifical skin or other dressings applicable to the healing of burns and wounds. The second layer performs the function of keeping bacteria out of the wound site while allowing water to evaporate through it at about the same rate as normal epidermis. This outer layer should possess comparable strength and elasticity to that of healthy skin. Materials having these properties are disclosed, for example, in British Patent Specification No. 1518748.

Antibacterial or other therapeutic agents may be incorporated in dressings according to the invention.

The following examples describe wound dressings incorporating complexes according to the present invention.

EXAMPLE 4

A burn dressing was formed from the following three layers:
1. A wound contact layer consisting of a collagen/alginate film prepared according to Example 1, without crosslinking.
2. An intermediate layer consisting of activated charcoal cloth.
3. An outer layer comprising a moisture vapour permeable polyurethane film. Such film is described in British Patent Specification No. 1280631.

This type of dressing is designed to be changed frequently, for example every four to five hours, and a fairly rapid rate of biodegradation of the collagen/aliginate layer is therefore permissible.

Silver sulphadiazene may be incorporated as a bacteriacide in the wound contact layer.

EXAMPLE 5

A burn dressing is formed from the following two layers:
1. A wound contact layer comprising a dehydrothermally crosslinked collagen/alginate film.
2. An outer layer of moisture vapour permeable polyurethane film as described in Example 4 above.

This dressing is designed to function as an artificial skin, and will therefore remain in place for a period of 4 to 6 weeks. A lower rate of biodegradation is therefore necessary, and a crosslinked complex is therefore used. Also, since the collagen/alginate layer should not represent a significant barrier to the passage of moisture vapour, a pore size of 100 microns is appropriate.

Silver sulphadiazene may also be incorporated in the wound contact layer of this dressing.

It will be appreciated that many other forms of dressing may be formed with the complex of the present invention. For example, dressings may be formed incorporating electrically conducting layers for the electrical stimulation of wound healing, or the complex of the present invention may be used as a wound contact layer in conjunction with conventional absorbents.

We claim:

1. A process for forming a porous protein/polysaccharide complex, said process comprising treating a solution containing less than 2% w/v of a biodegradable protein, or a hydrolytic degradation product thereof, with a polyanionic plant polysaccharide at a pH which is no higher than the isoelectric pH of said protein or degradation product to precipitate the complex and freeze-drying the complex.

2. A process according to claim 1, wherein the biodegradable protein is collagen.

3. A process according to claim 1 wherein the polysaccharide is an alginate.

4. A process according to claim 3, wherein said solution contains less than 1% w/v.

5. A process according to claim 4, wherein said solution contains less than 0.5% w/v.

6. A process according to claim 5, wherein said solution contains from 0.3 to 0.35% w/v.

7. A process according to claim 1 wherein the protein constitutes from 50 to 99% by weight of the complex.

8. A process according to claim 7 wherein the protein constitutes from 50 to 80% by weight of the complex.

9. A process according to claim 1 wherein said complex is blast frozen prior to said freeze-drying step.

10. A porous complex of a biodegradable protein, or a proteolytic degradation product thereof, with a polyanionic plant polysaccharide, and having a pore size greater than 20 microns.

11. A complex according to claim 10 wherein said protein is collagen.

12. A complex according to claim 10 wherein the polysaccharide is an alginate.

13. A complex according to claim 10 having a pore size greater than 50 microns.

14. A complex according to claim 13 having a pore size greater than 100 microns.

* * * * *